United States Patent [19]
Lange et al.

[11] Patent Number: 6,077,258
[45] Date of Patent: *Jun. 20, 2000

[54] BRAIDED ANGIOGRAPHY CATHETER HAVING FULL LENGTH RADIOPACITY AND CONTROLLED FLEXIBILITY

[75] Inventors: Michael R. Lange, St. Paul; Henry J. Pepin, Loretto, both of Minn.

[73] Assignee: SciMed Life Systems, Inc., Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/943,628

[22] Filed: Oct. 3, 1997

[51] Int. Cl.⁷ .................................................. A61M 25/00
[52] U.S. Cl. ...................... 604/527; 604/523; 604/525; 604/524; 604/264
[58] Field of Search .................... 604/523–527, 604/529, 264; 138/123–125, 137, 140, 141, 144, 145

[56] References Cited

U.S. PATENT DOCUMENTS

| | | | |
|---|---|---|---|
| 2,857,915 | 10/1958 | Sheridan | 128/349 |
| 3,070,132 | 12/1962 | Sheridan | 138/118 |
| 3,485,234 | 12/1969 | Stevens | 128/2 |
| 3,529,633 | 9/1970 | Vaillancourt | 138/118 |
| 3,605,750 | 9/1971 | Sheridan et al. | 128/348 |
| 3,608,555 | 9/1971 | Greyson | 128/348 |
| 3,618,614 | 11/1971 | Flynn | 128/348 |
| 3,749,134 | 7/1973 | Slingluff et al. | 138/177 |
| 3,888,249 | 6/1975 | Spencer . | |
| 3,962,153 | 6/1976 | Gore | 260/2.5 R |
| 4,027,659 | 6/1977 | Slingluff | 128/2 M |
| 4,277,432 | 7/1981 | Woinowski | 264/173 |
| 4,282,876 | 8/1981 | Flynn | 128/349 R |
| 4,283,447 | 8/1981 | Flynn | 428/36 |
| 4,318,402 | 3/1982 | Vaillancourt | 128/214.4 |
| 4,321,226 | 3/1982 | Markling | 264/139 |
| 4,402,684 | 9/1983 | Jessup | 604/264 |
| 4,425,919 | 1/1984 | Alston, Jr. et al. | 128/658 |
| 4,430,083 | 2/1984 | Ganz et al. | 604/283 |
| 4,469,483 | 9/1984 | Becker et al. | 604/280 |
| 4,516,970 | 5/1985 | Kaufman et al. | 604/270 |
| 4,516,972 | 5/1985 | Samson | 604/282 |
| 4,563,181 | 1/1986 | Wijayarathna et al. | 604/280 |
| 4,568,338 | 2/1986 | Todd | 604/281 |
| 4,577,543 | 3/1986 | Wilson | 87/11 |
| 4,588,399 | 5/1986 | Nebergall et al. | 604/280 |
| 4,596,563 | 6/1986 | Pande | 604/264 |

(List continued on next page.)

OTHER PUBLICATIONS

Johnson, "Paste Extrusion of Filled TFE–Fluorocarbon Resin for Wire Insulations", *SPE Journal*, Feb., 1961, pp. 151–154.

"Tetrafluoroethylene Polymers", *Encyclopedia of Polymer Science and Technology*, vol. 13, Copyright 1970, John Wiley & Sons, Inc., pp. 623–654.

Carlson et al., *Fluoropolymers, Organic*, vol. A11, Copyright 1988, Verlagsgesellschaft mbH, Weinheim, Germany, pp. 393–428.

Lonz et al., "Extrusion Properties of Lubricated Resin from Coagulated Dispersion", *Industrial and Engineering Chemistry*, vol. 44, No. 8, Aug. 1952, pp. 1805–1810.

*Primary Examiner*—Wynn Wood Coggins
*Assistant Examiner*—Cris L. Rodriguez
*Attorney, Agent, or Firm*—Crompton, Seager & Tufte, LLC

[57] ABSTRACT

A guiding catheter or angiographic catheter for use in cardiovascular interventions which incorporates a low-flexibility multi-layer proximal zone wherein a transition zone separates the proximal zone and a high flexibility distal zone. A mid-region zone transitions the high stiffness of the proximal zone to the higher flexibility of the distal zone to eliminate buckling and kinking. All zones of the catheter have a sufficiently large and substantially similar radiopacity, which allows the entirety of the catheter to be visible in a fluoroscope or other form of x-ray so that the positioning of the catheter can be precisely determined.

14 Claims, 1 Drawing Sheet

U.S. PATENT DOCUMENTS

| | | | |
|---|---|---|---|
| 4,636,346 | 1/1987 | Gold et al. | 264/139 |
| 4,657,024 | 4/1987 | Coneys | 128/658 |
| 4,661,094 | 4/1987 | Simpson | 604/53 |
| 4,665,604 | 5/1987 | Dubowik | 29/415 |
| 4,690,175 | 9/1987 | Ouchi et al. | 138/131 |
| 4,735,620 | 4/1988 | Ruiz | 604/281 |
| 4,739,768 | 4/1988 | Engelson | 128/658 |
| 4,764,324 | 8/1988 | Burnham | 264/103 |
| 4,784,638 | 11/1988 | Ghajar et al. | 604/49 |
| 4,806,182 | 2/1989 | Rydell et al. | 156/211 |
| 4,817,613 | 4/1989 | Jaraczewski et al. | 128/658 |
| 4,838,879 | 6/1989 | Tanabe et al. | 604/280 |
| 4,842,590 | 6/1989 | Tanabe et al. | 604/282 |
| 4,863,442 | 9/1989 | DeMello et al. | 604/282 |
| 4,882,392 | 11/1989 | Smid et al. | 525/328.6 |
| 4,886,506 | 12/1989 | Lovgren et al. | 604/280 |
| 4,898,591 | 2/1990 | Jang et al. | 604/282 |
| 4,925,710 | 5/1990 | Buck et al. | 428/34.5 |
| 4,961,731 | 10/1990 | Bodicky et al. | 604/264 |
| 4,963,306 | 10/1990 | Weldon | 264/101 |
| 4,968,307 | 11/1990 | Dake et al. | 604/264 |
| 5,019,057 | 5/1991 | Truckai | 604/264 |
| 5,021,044 | 6/1991 | Sharkawy | 604/53 |
| 5,037,403 | 8/1991 | Garcia | 604/280 |
| 5,045,072 | 9/1991 | Castillo et al. | 604/280 |
| 5,057,092 | 10/1991 | Webster, Jr. | 604/282 |
| 5,061,257 | 10/1991 | Martinez et al. | 604/282 |
| 5,069,673 | 12/1991 | Shwab | 604/280 |
| 5,078,702 | 1/1992 | Pomeranz | 604/280 |
| 5,085,863 | 2/1992 | Goshiki | 424/423 |
| 5,088,991 | 2/1992 | Weldon | 604/280 |
| 5,160,559 | 11/1992 | Scovil et al. | 156/73.6 |
| 5,171,232 | 12/1992 | Castillo et al. | 604/280 |
| 5,199,950 | 4/1993 | Schmitt et al. | 604/95 |
| 5,201,723 | 4/1993 | Quinn | 604/264 |
| 5,221,270 | 6/1993 | Parker | 604/282 |
| 5,234,416 | 8/1993 | Macaulay et al. | 604/282 |
| 5,254,107 | 10/1993 | Soltesz | 604/282 |
| 5,256,158 | 10/1993 | Tolkoff et al. | 604/280 |
| 5,279,596 | 1/1994 | Castaneda et al. | 604/282 |
| 5,300,048 | 4/1994 | Drewes, Jr. et al. | 604/280 |
| 5,306,263 | 4/1994 | Voda | 604/281 |
| 5,318,032 | 6/1994 | Lonsbury et al. | 128/658 |
| 5,335,410 | 8/1994 | Brunham | 29/452 |
| 5,358,493 | 10/1994 | Schweich, Jr. et al. | 604/264 |
| 5,389,090 | 2/1995 | Fischell et al. | 604/280 |
| 5,399,164 | 3/1995 | Snoke et al. | 604/95 |
| 5,401,258 | 3/1995 | Voda | 604/281 |
| 5,403,292 | 4/1995 | Ju | 604/282 |
| 5,425,723 | 6/1995 | Wang | 604/280 |
| 5,433,713 | 7/1995 | Trotta | 604/264 |
| 5,441,489 | 8/1995 | Utsumi et al. | 604/280 |
| 5,445,624 | 8/1995 | Jimenez | 604/280 |
| 5,472,435 | 12/1995 | Sutton | 604/282 |
| 5,489,277 | 2/1996 | Tolkoff et al. | 604/280 |
| 5,509,910 | 4/1996 | Lunn | 604/282 |
| 5,514,236 | 5/1996 | Avellanet et al. | 156/154 |
| 5,531,685 | 7/1996 | Hemmer et al. | 604/95 |
| 5,531,721 | 7/1996 | Pepin et al. | 604/282 |
| 5,533,985 | 7/1996 | Wang | 604/246 |
| 5,538,512 | 7/1996 | Zenzon et al. | 604/280 |
| 5,538,513 | 7/1996 | Okajima | 604/282 |
| 5,542,924 | 8/1996 | Snoke et al. | 604/95 |
| 5,542,937 | 8/1996 | Chee et al. | 604/280 |
| 5,545,149 | 8/1996 | Brin et al. | 604/265 |
| 5,545,151 | 8/1996 | O'Connor et al. | 604/282 |
| 5,554,139 | 9/1996 | Okajima | 604/282 |
| 5,569,200 | 10/1996 | Umeno et al. | 604/96 |
| 5,569,218 | 10/1996 | Berg | 604/282 |
| 5,569,220 | 10/1996 | Webster, Jr. | 604/282 |
| 5,584,821 | 12/1996 | Hobbs et al. | 604/280 |
| 5,599,319 | 2/1997 | Stevens | 604/264 |
| 5,599,325 | 2/1997 | Ju et al. | 604/282 |
| 5,599,326 | 2/1997 | Carter | 604/282 |
| 5,603,705 | 2/1997 | Berg | 604/282 |
| 5,614,136 | 3/1997 | Pepin et al. | 264/40.3 |
| 5,658,263 | 8/1997 | Dang et al. | 604/280 |
| 5,662,621 | 9/1997 | Lafontaine | 604/281 |
| 5,662,622 | 9/1997 | Gore et al. | 604/282 |
| 5,674,208 | 10/1997 | Berg et al. | 604/282 |
| 5,676,659 | 10/1997 | McGurk | 604/282 |
| 5,680,873 | 10/1997 | Berg et al. | 128/772 |
| 5,695,483 | 12/1997 | Samson | 604/282 |
| 5,702,373 | 12/1997 | Samson | 604/282 |
| 5,755,704 | 5/1998 | Lunn | 604/282 |
| 5,782,811 | 7/1998 | Samson et al. | 604/282 |
| 5,836,926 | 11/1998 | Peterson et al. | 604/282 |
| 5,851,226 | 12/1998 | Skubitz et al. | 607/126 |
| 5,853,400 | 12/1998 | Samson | 604/282 |
| 5,860,963 | 1/1999 | Azam et al. | 604/280 |
| 5,868,718 | 2/1999 | Pepin et al. | 604/264 |
| 5,876,385 | 3/1999 | Ikari et al. | 604/280 |
| 5,891,112 | 4/1999 | Samson | 604/282 |
| 5,906,606 | 5/1999 | Chee et al. | 604/527 |
| 5,908,413 | 6/1999 | Lange et al. | 604/529 |
| 5,911,715 | 6/1999 | Berg et al. | 604/525 |
| 5,938,653 | 8/1999 | Pepin | 604/527 |

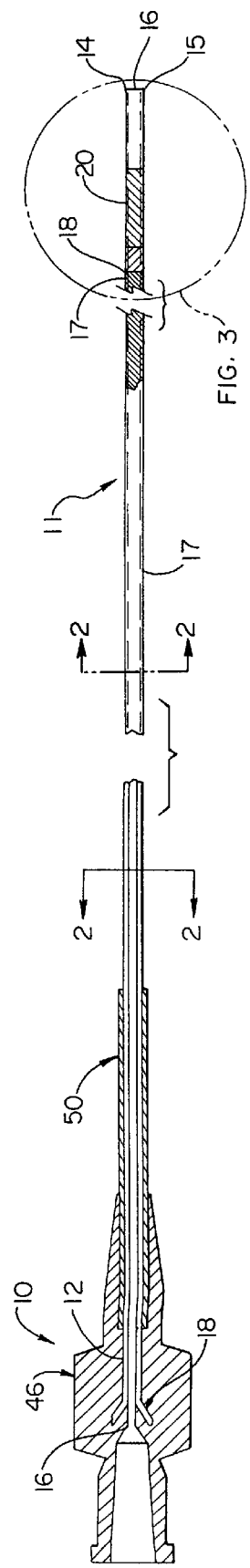
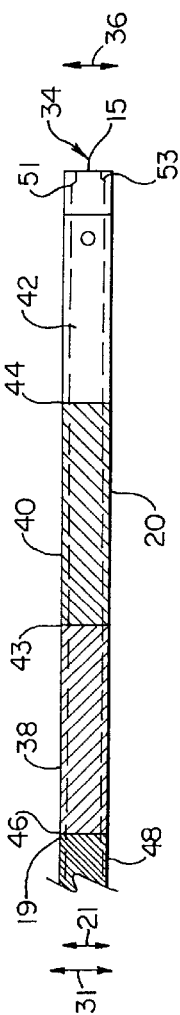
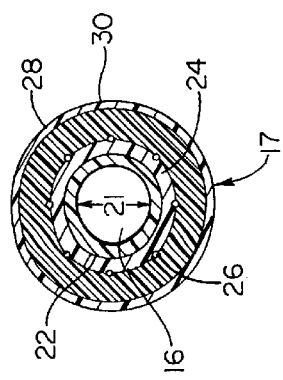

BRAIDED ANGIOGRAPHY CATHETER HAVING FULL LENGTH RADIOPACITY AND CONTROLLED FLEXIBILITY

TECHNICAL FIELD

This invention relates to the field of intravascular medical devices, and more particularly, to the field of catheters such as angiographic and guide catheters used for the placement of medicines and medical devices within the body. Specifically, the invention is directed to an improved guide or diagnostic catheter having full length radiopacity incorporating a proximal zone having lower flexibility than a distal zone, where a transition zone provides varying flexibility between the proximal zone and is the distal zone for improved catheter performance.

BACKGROUND OF THE INVENTION

Angiographic and guide catheters are well known in the field of medicine for use in conjunction with other catheters for the treatment of cardiovascular disease through such procedures as percutaneous transluminal coronary angioplasty (PTCA) procedures. Guide catheters aid in treatment of arterial lesions by providing a conduit for positioning dilatation balloon systems across an arterial stenosis. The need for a greater variety of guide catheters to treat different types of circumstances has grown tremendously as the techniques for the use of such devices has grown.

During the treatment of cardiovascular disease, the catheter must be able to traverse tortuous pathways through blood vessels in a manner that minimizes trauma. In order for the physician to place the catheter at the correct location in the vessel, the physician must apply longitudinal and rotational forces. The catheter must be stiff enough to resist the formation of kinks, while at the same time, the catheter must possess flexibility to be responsive to maneuvering forces when guiding the catheter through the vascular system. The catheter must be rigid enough to push through the blood vessel, but yet flexible enough to navigate the bends in the blood vessel. The guide or angiographic catheter must exhibit good torque control such that manipulation of a proximal portion of the catheter is responsively translated to the tip or distal end of the catheter to curve and guide the catheter through the tortuous pathways. Thus, the catheter must have torsional rigidity to transmit the applied torque. To accomplish this, balance between longitudinal rigidity, torsional rigidity and flexibility, often times a support member is added to the shaft. This support member is often comprised of a metal braid or a coil embedded in the shaft.

In many applications, the catheter is guided through the aorta over the aortic arch and down to the ostium of the vessel which is to be treated. It is preferable to have a soft tip or flexible section engage the ostium. Therefore, it is advantageous to have the proximal section more rigid to transmit the forces applied, but have the distal end more flexible to allow for better placement of the catheter. Having the distal section more flexible also creates a less traumatic section to contact the blood vessel. The distal end of the catheter is rotated, through the transmission of torque from the proximal end, until the tip of the catheter is in the desired position. With the variation of different bend shapes available on the distal ends of these devices and with variations in patient anatomy, each device may need to be torqued more or less in order to correctly place it.

In order to meet these performance requirements, catheters are often manufactured using polymers in conjunction with the above-mentioned support member using a metal braid or coil, wherein the support member is incorporated into the tube of the guide catheter. Catheters can be formed of three layers. An inner tubular member is used which defines an inner lumen which may be formed of a material that decreases the coefficient of friction such as that encountered between a balloon catheter and the inner lumen of the catheter. The support member conforms to the outside of the inner layer and is often comprised of a metal braid or coil. The third outer tube is commonly formed from a polymer and overlays the support member.

In order to meet the above requirements of rigidity and flexibility, a catheter is desired which has regions of varying stiffness which may be readily changed during manufacturing to meet the need for the greater variety of devices necessary to treat different types of circumstances.

An example of one approach is described in U.S. Pat. No. 5,533,985, issued Jul. 9, 1996 to James C. Wang, for Tubing, which is incorporated herein by reference. Wang discloses differential stiffness tubing for medical products, including catheters, wherein the tubing has a stiff section and a flexible section joined by a relatively short transition section in which the materials of the stiff and flexible sections are joined into each other in a smooth gradual manner to produce an inseparable bond between the materials without abrupt joints. This tubing is manufactured using an extrusion process and may be limited in its ability to manufacture catheters having the desired number of regions of varying stiffness and the ability to easily accommodate product design changes during manufacture.

Catheters may be manufactured using this approach, but its practical application may be limited to joining two materials to form two zones of flexibility with a transition therebetween. Thus, with this approach, additional manufacturing steps are necessary to provide for additional regions. These regions of varying stiffness are necessary to provide rigidity to push the catheter through the blood vessel, flexibility to navigate the bends in the blood vessel, and torsional stiffness to correctly place the catheter by maintaining torque control without excessive energy storage which can cause undesirable movement of the catheter end.

It is advantageous that the catheter be visible in a fluoroscope or other form of x-ray, so that the catheter can be positioned with precision. In the prior art, this has been accomplished by applying a metal ring to the catheter adjacent the distal end. It is generally undesirable to place the metal ring exactly on the distal tip of the catheter, since the distal tip needs to be very soft and pliable. Therefore, the metal ring does not completely resolve the problem of precisely locating the distal tip of the catheter within the body by means of a fluoroscope during a medical procedure, since the metal ring is and must. be spaced from the distal tip. In other prior art, the distal tip has been manufactured to be substantially more radiopaque than portions of the catheter proximal to the tip.

SUMMARY OF THE INVENTION

The present invention overcomes many of the disadvantages found in the prior art by providing a guiding catheter for use in coronary angioplasty and other cardiovascular interventions which incorporates a lower flexibility proximal shaft portion, coupled to a higher flexibility distal tip portion. Within the distal tip, there are three distinct zones of flexibility. A tip transition portion separates a proximal tip portion from a distal tip portion. The transition portion gradually transitions the lower flexibility of the proximal portion to a higher flexibility of the distal portion via a gradual transition in materials from a higher durometer polymer to a lower durometer polymer to eliminate buckling and kinking. Therefore, when including the flexibility of the proximal shaft portion, the catheter of the present invention includes four distinct zones of flexibility.

The catheter also possesses a high level of radiopacity, said level being substantially similar throughout all portions of the device. It is particularly desirable for all portions of the device to be visible in a fluoroscope or other form of x-ray so that the positioning of the catheter can be precisely determined.

In a preferred embodiment of the present invention, a guide or angiographic catheter is provided comprising a linear shaft and a lumen extending longitudinally through the center of the linear shaft. The linear shaft is comprised of a proximal shaft portion of high radiopacity at the proximal end of the linear shaft, and a distal tip of high radiopacity which extends distally from the distal end of the proximal shaft portion to the distal end of the linear shaft. The distal tip is attached to the distal end. of the proximal shaft portion by heat bonding. The radiopacity of all portions of the linear shaft is substantially similar.

The proximal shaft portion further comprises an inner tubular member defining the diameter of the center lumen, an intermediate tubular member overlying and conforming to the inner tubular member, a woven braid member overlying and conforming to the intermediate tubular member, an outer tubular member substantially overlying and conforming to the woven braid member and an outer sleeve tubular member substantially overlying and conforming to the outer tubular member.

The distal tip further comprises a proximal portion having a first material of a first stiffness, a transition portion having a second material with a continuous differential second stiffness, and a distal portion having a third material of a third stiffness. The first stiffness of the first material will be larger than the third stiffness of the third material. The second stiffness of the second material is defined by a gradual transition from the stiffness of the first material of the proximal portion of the distal tip to the stiffness of the third material of the distal portion of the distal tip.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a plan view with the manifold cross sectioned of a catheter showing a preferred embodiment of the present invention;

FIG. 2 is a cross section view of FIG. 1 taken along line 2—2;

FIG. 3 is a plan view of the distal tip area of the catheter of FIG. 1, illustrating the shaft/tip heat bonding site and the portions of the distal tip including a transition zone of varying stiffness.

DETAILED DESCRIPTION OF THE PREFERRED EMBODIMENTS

Referring now to the drawings, wherein like reference numerals refer to like elements throughout the several views, FIG. 1 is a plan view of a catheter with the manifold shown in cross section showing a preferred embodiment of the present invention. FIG. 1 shows a catheter 10 which comprises a hub 46, and a linear shaft 11 having a proximal end 12 and a distal end 14. A central lumen 16 extends longitudinally through the linear shaft from the proximal end 12 to the distal end 14. The linear shaft 11 comprises a proximal shaft 17 and a distal tip 20. The proximal shaft: 17 has a proximal end 18 and a distal end 19. The distal tip 20 is attached to the distal end 19 of the proximal shaft 17 at the shaft/tip heat bonding site 48.

Referring now to FIG. 2, the proximal shaft portion 17 includes an inner tubular member 22 formed from polyurethane which extends from the proximal end 18 to the distal end 19 of the proximal shaft 17. The inner tubular member 22 defines the inner diameter 21 of the central lumen 16. An intermediate tubular member of polyether block amide copolymer (PERA) 24, commercially available under the trademark PEBAX, is extruded over the entire length of the inner tubular member 22. The intermediate tubular member of PEBAX 24, has a durometer of 67 D, is 80% loaded with a Tungsten filler and a 1% UV stabilizer.)

A woven braid member 26 is provided over the entire length of the intermediate tubular member 24. In one embodiment, the intermediate tubular member 24 and woven braid member 26 are passed through a heated dye so that the woven braid member 26 is slightly embedded in the outer surface of the intermediate tubular member 24. In a second embodiment, the intermediate tubular member 24 is substantially cooled before the woven braid member 24 is provided so that the woven braid member 26 is not embedded in the outer surface of the intermediate tubular member 24. The woven braid member 26 is preferably braided from strands of round 0.0020" annealed 304 stainless steel, and has a constant braid density of 40 pic/in over the length of the proximal shaft portion 17.

An outer tubular member 28 is extruded over the entire length of the woven braid member 26. The outer tubular member 28 is preferably manufactured from PEBAX and has a durometer of 67 D, is 80% loaded with a Tungsten filler and a 1% UV stabilizer, and is not translucent. An outer sleeve tubular member of PEBAX 30 is extruded over the entire length of the outer tubular member of PEBAX 28. The outer sleeve tubular member of PEBAX has a durometer of 70 D, and is 30% loaded with a bismuth subcarbonate filler and a colorant (phthalocyanine blue and violet 23).

Referring now to FIG. 3, the distal tip 20 is attached to the distal end 19 of the proximal shaft portion 17 by a heat bonding process. The distal tip 20 has a lumen 34 extending therethrough which defines the central lumen 16 in the distal portion 15. The inner diameter of the tip lumen 36 defined by the distal tip 20 is substantially equal to the inner diameter of the lumen 21 defined by the inner layer of polyurethane 22 of the proximal shaft portion 17. The very distal end of the tip 53 is tapered and the inner diameter within the very distal end of the tip 53 is smaller to fit tightly over a guide wire.

The distal tip 20 is formed from PEBAX using an Interrupted Layer Coextrustion (ILC) process, which in preferred embodiments results in a proximal portion 38, a transition portion 40, a distal portion 42, and a distal end of distal tip 51. The proximal portion 38, transition portion 40, and distal portion 42 preferably have linear dimensions of about 1.25", 1.5" and 1.25", respectively, resulting in a total linear dimension of about 4".

The proximal portion 38 of the distal tip 20 has a durometer of 70 D, and is 55% loaded with a Tungsten filler and a 1% UV stabilizer. The distal portion 42 has a durometer of 47 D, and is also 55% loaded with a Tungsten filler and a 1% UV stabilizer. The transition portion 40 has a durometer ranging from 70 D at the proximal end 43 to 47 D at the distal end 44, as provided by the ILC process. Experiments show that the proximal shaft portion 17 has substantially the same radiopacity as the distal tip 20.

Referring back to FIG. 1, the proximal end 18 of the proximal shaft portion 17 extends into a hub 46 molded directly over the proximal shaft portion 17. A 63 D white PEBAX strain relief is insert molded to the hub, and the proximal shaft portion 17 extends into the hub 46 through the PEBAX strain relief 50.

Having thus described the preferred embodiments of the present invention, those of skill in the art will readily appreciate that yet other embodiments may be made and used within the scope of the claims hereto attached.

What is claimed is:

1. A tubular assembly for an intravascular catheter comprising:
    a linear shaft having a proximal end, a distal end, and a lumen extending longitudinally therethrough;
    a proximal shaft portion of high radiopacity included within said linear shaft, said proximal shaft portion extending distally a predefined distance from the proximal end of said linear shaft, wherein said proximal shaft portion has a proximal end and a distal end;
    an inner tubular member contained within said proximal shaft portion;
    an intermediate tubular member overlying said inner tubular member and conforming thereto;
    a woven braid member overlying said intermediate tubular member and conforming thereto;
    an outer tubular member substantially overlying said woven braid member, said outer tubular member having a radiopaque agent dispersed therein;
    an outer sleeve overlying at least a portion of said outer tubular member; and
    a distal tip included within said linear shaft extending distally from the distal end of said proximal shaft portion to the distal end of said linear shaft, said distal tip comprising a proximal tip portion formed of a first material having a first flexibility higher that the flexibility of said proximal shaft portion, a distal tip portion formed of a second material having a second flexibility higher than said first flexibility of said proximal tip portion, and a transition portion between said proximal tip portion and said distal tip portion, formed of a material with a flexibility transitioning continuously from the lower flexibility of said proximal tip portion to the higher flexibility of said distal tip portion.

2. The tubular assembly of claim 1 wherein the inner tubular member is formed from polyurethane.

3. The tubular assembly of claim 1 wherein the intermediate tubular member is formed of polyether block amide, having a durometer of 67 D, 80% loaded with a Tungsten filler and a 1UV stabilizer.

4. The tubular assembly of claim 1 wherein the woven braid member is braided from strands of stainless steel.

5. The tubular assembly of claim 1 wherein said woven braid is embedded in outer surface of said intermediate tubular member.

6. The tubular assembly of claim 1 wherein said intermediate tubular member is substantially cooled before said woven braid member is provided so that said woven braid is not embedded in outer surface of said intermediate tubular member.

7. The tubular assembly of claim 1 wherein said outer tubular member is formed of polyether block amide having a durometer of 67 D, is 80% loaded with a Tungsten filler and a 1% UV stabilizer.

8. The tubular assembly of claim 1 wherein said outer sleeve tubular member substantially overlies all of said outer tubular member and conforming thereto.

9. The tubular assembly of claim 1 wherein said outer sleeve tubular member is formed from polyether block amide having a durometer of 70 D, and is 30% loaded with a bismuth subcarbonate filler and 1% colorant.

10. The tubular assembly of claim 1 wherein said distal tip is heat bonded to the distal end of said proximal shaft portion.

11. The tubular assembly of claim 1 wherein said distal tip is formed from polyether block amide.

12. The tubular assembly of claim 1 wherein said proximal tip portion, said transition portion, and said distal tip portion of said distal tip have linear dimensions of about 1.25", 1.5", and 1.25", respectively.

13. The tubular assembly of claim 1 wherein substantially all portions of said proximal shaft portion and said distal tip have substantially similar radiopacity.

14. The tubular assembly of claim 1 wherein said outer sleeve is less radiopaque than said outer tabular member.

* * * * *

UNITED STATES PATENT AND TRADEMARK OFFICE
CERTIFICATE OF CORRECTION

PATENT NO. : 6,077,258  
DATED : June 20, 2000  
INVENTOR(S) : Lange et al.

Page 1 of 1

It is certified that error appears in the above-identified patent and that said Letters Patent is hereby corrected as shown below:

<u>Column 6,</u>
Line 11, change "and a 1UV stabilizer" to --and a 1% UV stabilizer--.
Line 46, change "outer tabular member" to --outer tubular member--.

Signed and Sealed this

Fourteenth Day of August, 2001

*Attest:*

*Attesting Officer*

NICHOLAS P. GODICI
*Acting Director of the United States Patent and Trademark Office*